US008235969B2

(12) United States Patent
Gregorich et al.

(10) Patent No.: US 8,235,969 B2
(45) Date of Patent: Aug. 7, 2012

(54) MEDICAL DEVICE SHAFT DESIGNS

(75) Inventors: Daniel Gregorich, St. Louis Park, MN (US); Soo-Young Yoon, Maple Grove, MN (US); Liza J. Davis, Maple Grove, MN (US); Tracee E. J. Eidenschink, Wayzata, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 837 days.

(21) Appl. No.: 11/276,554

(22) Filed: Mar. 6, 2006

(65) Prior Publication Data

US 2007/0208323 A1    Sep. 6, 2007

(51) Int. Cl.
*A61M 25/00* (2006.01)

(52) U.S. Cl. .................. 604/525; 604/103.09; 604/523; 604/524

(58) Field of Classification Search ............. 604/103.09, 604/282, 524, 525, 535, 523, 93.01, 273, 604/274, 541
See application file for complete search history.

(56) References Cited

U.S. PATENT DOCUMENTS

| | | | |
|---|---|---|---|
| 4,840,623 A | 6/1989 | Quackenbush | |
| 4,998,917 A | 3/1991 | Gaiser et al. | |
| 5,322,519 A | 6/1994 | Ash | |
| 5,496,292 A | 3/1996 | Burnham | |
| 5,497,785 A | 3/1996 | Viera | |
| 5,593,394 A | 1/1997 | Kanesaka et al. | |
| 5,647,846 A | 7/1997 | Berg et al. | |
| 5,792,144 A | 8/1998 | Fischell et al. | |
| 5,810,867 A | 9/1998 | Zarbatany et al. | |
| 5,882,347 A * | 3/1999 | Mouris-Laan et al. | ........ 604/524 |
| 5,897,536 A | 4/1999 | Nap et al. | |
| 5,902,254 A | 5/1999 | Magram | |
| 5,910,145 A | 6/1999 | Fischell et al. | |
| 5,951,494 A | 9/1999 | Wang et al. | |
| 5,976,153 A | 11/1999 | Fischell et al. | |
| 5,980,486 A | 11/1999 | Enger | |
| 6,036,654 A | 3/2000 | Quinn et al. | |
| 6,190,393 B1 | 2/2001 | Bevier et al. | |
| 6,248,092 B1 | 6/2001 | Miraki et al. | |
| 6,355,060 B1 | 3/2002 | Lenker et al. | |
| 6,475,184 B1 | 11/2002 | Wang et al. | |
| 6,623,491 B2 * | 9/2003 | Thompson | ..................... 606/108 |
| 6,623,518 B2 | 9/2003 | Thompson et al. | |
| 6,712,807 B2 | 3/2004 | Stivland et al. | |

(Continued)

FOREIGN PATENT DOCUMENTS

| | | |
|---|---|---|
| JP | 09313613 A | 9/1997 |
| WO | 02/083224 A2 | 10/2002 |

*Primary Examiner* — Bhisma Mehta
*Assistant Examiner* — Larry R Wilson
(74) *Attorney, Agent, or Firm* — Seager, Tufte & Wickhem LLC

(57) ABSTRACT

Devices and methods for transferring forces down a catheter shaft while also maintaining an open fluid pathway are disclosed. In some of the designs, inner and outer members of the catheter interact, allowing improved transfer of forces down the catheter shaft. These designs also allow for maintenance of a fluid pathway along the length of the shaft, including at locations where the inner and outer members are interacting with one another. Structures are disclosed which extend at least a portion of the length of the shaft, allowing improved force transfer and resistance to kinking. Structures are also disclosed which specifically allow for inner and outer members to engage one another at at least one point along the shaft, improving the transfer of forces down the shaft.

12 Claims, 11 Drawing Sheets

U.S. PATENT DOCUMENTS

| | | |
|---|---|---|
| 6,786,918 B1 | 9/2004 | Krivoruchko et al. |
| 2002/0095203 A1* | 7/2002 | Thompson et al. .......... 623/1.11 |
| 2004/0147914 A1 | 7/2004 | Kramer |
| 2005/0049609 A1 | 3/2005 | Gunderson et al. |
| 2005/0102020 A1* | 5/2005 | Grayzel et al. ............... 623/1.11 |
| 2005/0124918 A1 | 6/2005 | Griffin et al. |
| 2006/0235502 A1* | 10/2006 | Belluche et al. ............. 623/1.11 |

* cited by examiner

MEDICAL DEVICE SHAFT DESIGNS

FIELD OF THE INVENTION

The present invention relates generally to the field of intracorporeal devices, including medical devices that are used for the transfer of fluids into, out of, or between locations within a patient's anatomy.

BACKGROUND OF THE INVENTION

Elongated medical devices such as catheters are used in a wide variety of medical procedures. Many of these procedures require fluid transfer, for example from one portion of a patient's body to another, from outside to inside the patient, or for removal of fluids from a patient's body. Examples of such therapeutic procedures include infusion or irrigation, aspiration of bodily fluids, and perfusion, along with many other procedures that benefit from fluid communication through a medical device.

Some fluid transfer procedures involve the use of balloon catheters. Balloon catheters are used to perform angioplasty, for temporarily blocking blood vessels, and for deploying stents, among other uses. In order to facilitate inflation and deflation of the balloon, balloon catheters typically have the ability to transport fluids to and from the balloon, often through a fluid flow lumen.

In addition, many intracorporeal procedures require devices to travel significant lengths through tortuous pathways in a patient's body. Such applications require the catheter shaft to have both strength and flexibility. A catheter shaft can be subjected to many different forces: for example, axial or torsional, or other forces that can cause the shaft to bend and/or kink. Catheters with fluid flow lumens are often subject to all of these forces while also being used for fluid transfer.

Medical devices with fluid flow lumens often comprise an inner and an outer member. In order to provide for a stronger shaft, some designs have used inner members with larger outer diameters. This can add overall strength to the shaft (thicker shaft walls can lead to higher strength) and can also make the clearance between the inner surface of the outer member and the outer surface of the inner member smaller. When forces act on such a shaft design, the inner member can come in contact with the outer member, and the two members together can yield more shaft strength and resistance to kinking than either member might separately provide. With less clearance between the inner and outer members, less relative movement is required to cause them to come into contact, thus providing a shaft that can be strong and kink resistant. However, designs in which the outer diameter of the inner member is made larger can cause a blockage or restriction of the fluid flow lumen, eliminating or restricting the ability to transfer fluids through the shaft.

SUMMARY OF THE INVENTION

The present invention relates generally to the field of intracorporeal devices, including medical devices that are used for the transfer of fluids into, out of, or between locations within a patient's anatomy. An exemplary embodiment of the present invention comprises an elongated shaft (e.g., a catheter shaft), which comprises inner and outer elongate members. A space between these elongate members can define a lumen that can be used for fluid flow. In one embodiment, the fluid flow lumen allows a distal balloon to be in fluid communication with a fluid source.

In one example of the invention, the inner member of the shaft can have raised portions, such as splines, running down at least a portion of the length of the inner member. The raised portions can provide increased shaft strength and increased resistance to kinking. The raised portions could also be placed on the inner surface of the outer member. In addition, the raised portions can be placed on both the outer surface of the inner member and the inner surface of the outer member. Further, the inner and outer raised portions can interact with one another, facilitating the transfer of torsional forces down the length of the shaft. Any of these examples can include a design of the raised portions such that a fluid flow pathway is maintained between the inner and outer members, even through areas where the inner and outer members are in contact with one another.

In other embodiments, the inner and outer members can interact in other ways to transfer forces down the shaft while also maintaining an open fluid flow lumen. In one embodiment, the shaft has an inner member, an outer member, and a transition area. The inner diameter of the outer member transitions from a relatively small inner diameter proximal of the transition area to a relatively large inner diameter distal of the transition area. The inner member can change from a relatively small outer diameter proximal of the transition area to a relatively thick outer diameter distal of the transition area. The transition of the outer member can create an outer force transfer surface and the transition of the inner member can create an inner force transfer surface. When forces are imparted on the shaft that make the inner and outer members move longitudinally relative to one another, these two force transfer surfaces can engage one another. This engagement can facilitate the transfer of forces down the shaft of the catheter. At the same time, cut-outs in the inner member, the outer member, or both, can be made in order to create a fluid flow pathway through the transition area. These cut-outs can ensure that an open fluid flow pathway will be maintained even when the force transfer surfaces are engaged and the fluid flow pathway might otherwise be sealed off or restricted.

In another embodiment, male threads are placed on the transition area of the outer surface of the inner member and female threads are placed on the transition area of the inner surface of the outer member. The engagement of the threads can cause an engagement of the inner and outer members, which can facilitate the transfer of forces down the shaft of the catheter. A fluid flow pathway can be maintained through the area occupied by the threads. One method of maintaining a fluid pathway is to design the teeth of the threads such that they do not fully engage one another. In this way, a spiral fluid flow pathway is left open along the thread pattern. Another possible method of maintaining an open fluid flow pathway is to place channels through the threads of the inner member, the outer member, or both.

An exemplary method of the current invention comprises the step of providing a catheter, such as, but not limited to, a catheter in accordance with any of the catheters described in this specification. The catheter can be advanced through the vasculature of a patient so that the distal end of the catheter is adjacent a treatment site. Alternatively, the catheter could be advanced over or in a guidewire or guide catheter that has already been advanced to, or near, the site of treatment. The catheter can then be used to deliver, remove, transfer or otherwise transport fluids by transferring fluids through the fluid flow lumen of the shaft. In one embodiment, the catheter is used to allow fluid communication between a balloon that is located near the distal end of the catheter and a fluid source coupled to a proximal portion of the catheter. The balloon could have a stent disposed on it, and inflation of the balloon could cause the stent to be deployed.

The above summary of some embodiments is not intended to describe each disclosed embodiment or every implementation of the present invention. The Figures, and Detailed Description which follows, more particularly exemplify some of these embodiments.

BRIEF DESCRIPTION OF THE DRAWINGS

The invention may be more completely understood in consideration of the following detailed description of various embodiments of the invention in connection with the accompanying drawings, in which.

Figure 1:
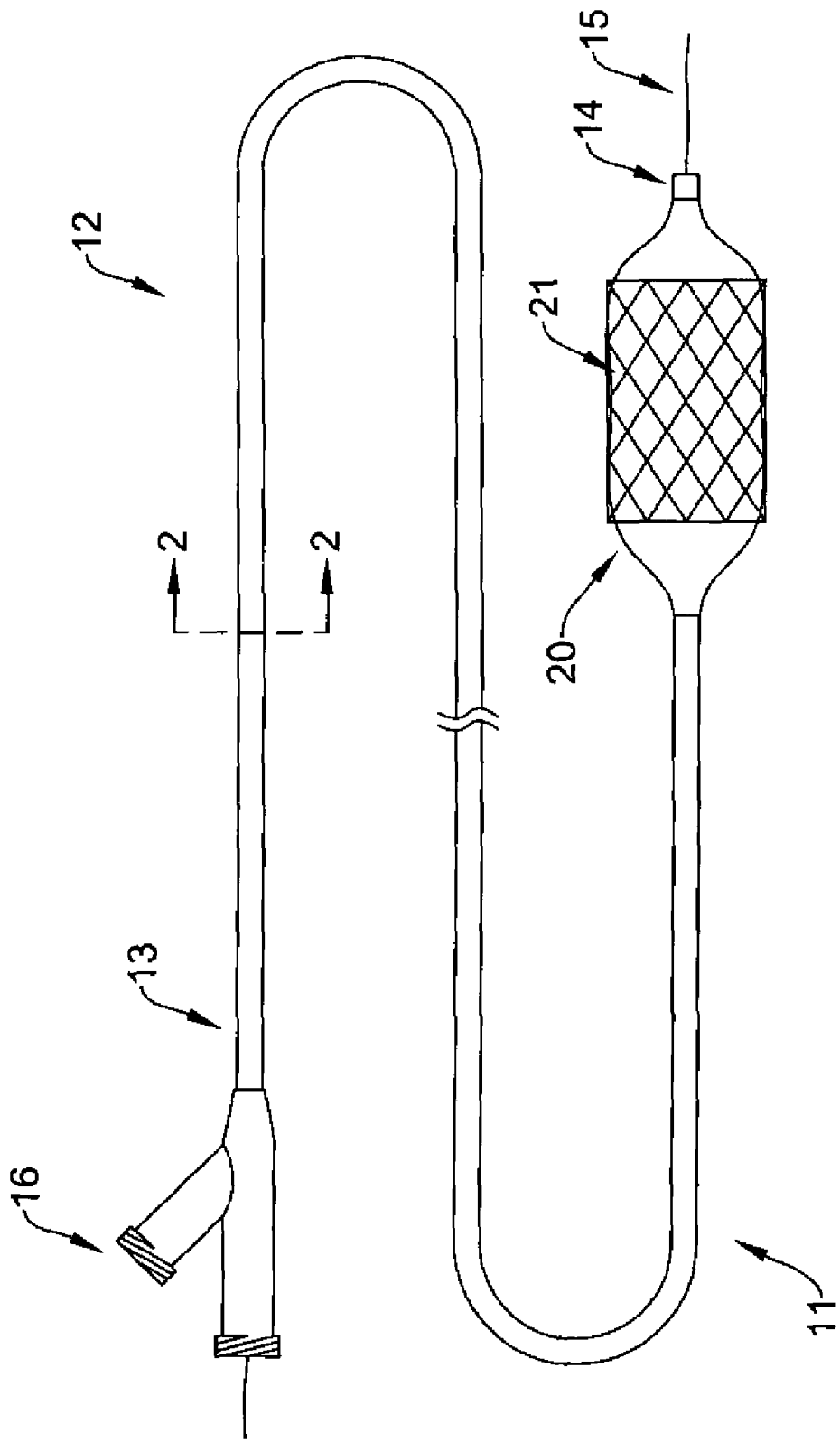
FIG. 1 is a perspective view of an embodiment of the current invention.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention.

DETAILED DESCRIPTION OF THE INVENTION

The following description should be read with reference to the drawings, in which like elements in different drawings are numbered in like fashion. The drawings, which are not necessarily to scale, depict selected embodiments and are not intended to limit the scope of the invention. Although examples of construction, dimensions, materials and manufacturing processes are illustrated for the various elements, those skilled in the art will recognize that many of the examples provided have suitable alternatives that may be utilized.

FIG. 1 is a perspective view of an example of a medical device 11 of the current invention. The medical device 11 has an elongate shaft 12, with a proximal end 13 and a distal end 14. The medical device 11 can also have a balloon 20 located near the distal end 14 of the medical device. In this example, the balloon is surrounded by a stent 21, and the balloon 20 can be used to deploy the stent 21. Such balloons can also be used for many other purposes, such as angioplasty procedures, or for temporarily blocking a vessel, or other procedures that are commonly known in the art. The elongate medical device 11 can also have a lumen (examples shown in later Figures) extending down the device that is designed to accommodate a guidewire 15. The guidewire 15 can be advanced to a location of interest within the patient's body, and the medical device 11 can then be advanced over the guidewire. Medical device 11 can also have a manifold 16 to facilitate positioning of the medical device 11 and for providing fittings for the introduction or removal of fluids.

Figure 2:
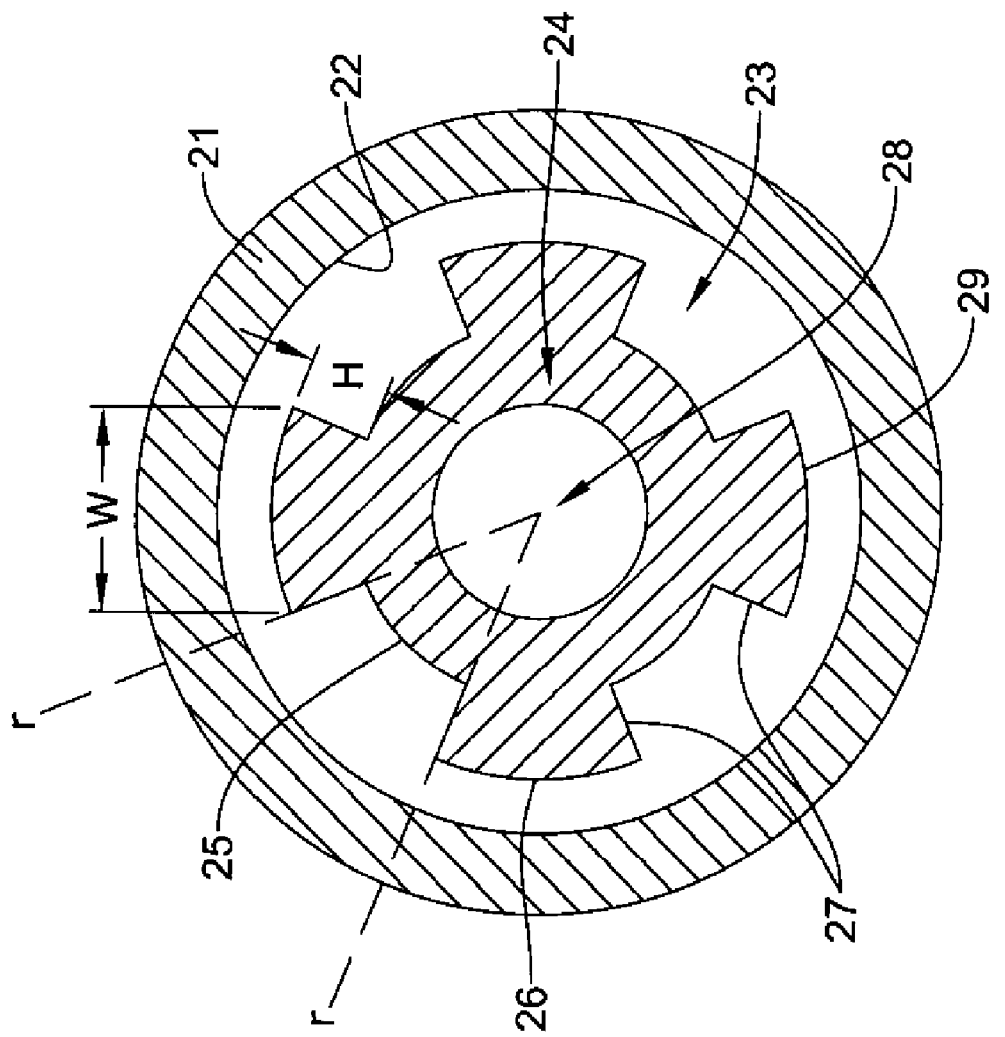
FIG. 2 is a cross-sectional view of a portion of the shaft of an embodiment with raised portions formed on the inner member.

FIG. 2 shows an axial cross-section of the shaft 12 of one embodiment of the medical device. The shaft has an outer member 21 and an inner member 24, and the space between these members defines a fluid flow lumen 23. The inner member 24 can also define a lumen 28, which can be used as a guidewire lumen, or for other purposes such as a second fluid flow lumen. The shaft can also define additional lumens, which can be used for alternate uses such as a fluid flow pathway, a lumen for introduction of an additional medical device, or other uses known in the art. These additional lumens can be defined by the inner member, by portions of the outer member, or by a space between the inner and outer members.

The outer surface 25 of the inner member can define raised portions (for example, raised portion 26), or splines. FIG. 2 shows that these raised areas can have tops 29 and sides 27 (for convenience, only one top and two of the sides of the raised portions are labeled in FIG. 2). The sides can be substantially aligned with radii that extend from the center of the shaft, as shown in FIG. 2. The raised areas 26 can effectively bring portions of the outer surface of the inner member in closer proximity to the inner surface of the outer member. When the shaft 12 is subjected to forces, the inner and outer members can move toward one another. With the raised areas 26 causing the inner and outer members to effectively be in close proximity, less movement may be required for the inner member to contact the outer member. In this way, the inner member and outer member can interact to support one another, which can yield a strong shaft that is resistant to kinking. At the same time, the space between the raised members can maintain an open fluid pathway (e.g., through the spaces between the raised portions 26), even if the shaft may become sharply bent or kinked.

The raised portions 26 have a width (W) and a height (H). When the shaft 12 does not have external forces acting on it, the fluid flow lumen 23 can be open substantially all the way around the inner member 24 (such as in a co-axial arrangement). Alternatively, the inner member could be in contact (or attached) to the outer member around portions of the circumference of the medical device. This could include the attachment of the inner and outer members at some or all of the raised portions, so the inner and outer members would not have to move relative to one another in order to interact.

As forces are placed on the shaft, or as the shaft is placed in a sharp bend of a patient's vasculature, the raised portions 26 and the inner surface 22 may move closer to one another, and can eventually contact as the forces increase and/or the sharpness of the bend increases. The contact can allow the inner and outer members to support one another, yielding a stronger shaft 12. Increasing the height (H) of the raised portion 26 can decrease the amount of force or the sharpness of the bend on the shaft before the raised portion 26 and the inner surface 22 contact one another.

In addition, the amount of surface area of the raised portion 26 that comes in contact with the inner surface 22 can also affect the interaction between the inner and outer members. In general, more surface contact between the raised portions 26 and the inner surface 22 can result in the inner and outer members providing one another more support, which can result in overall greater shaft strength. In this respect, other aspects of the raised portions 26 can be altered to provide for greater and more effective contact between the raised portions 26 and the inner surface 22. The tops 29 of the raised portion 26 could be flat or concave, or, as is shown in FIG. 2, the tops 29 could be curved convexly to closely match the curvature of the inner surface 22 of the outer member, which can allow more effective contact between the raised portions 26 and the inner surface 22. In other embodiments, the number of raised portions can also be varied in order to create more or less contact between the raised portions 26 and the inner surface 22. Also, the width (W) of the raised portions 26 can be increased or decreased depending on the amount of contact desired.

The raised portions 26 can extend down the entire length of the fluid flow lumen, or they can extend only for a part of the length. Portions of the inner member that do not have raised portions 26 can be round, oval or any other shape that provides the desired properties of the shaft 12. The raised portions can be positioned around the circumference of inner member at even intervals, or at some other interval. The number of raised portions 26 can also change from one longitudinal position to another. Portions of the inner member can have 1, 2, 3, 4, 5, 6, 7, 8, 9, or 10 raised portions 26. The dimensions (height or width, or other dimension) and/or shapes (flat, concave or convex surface, or other shape) of the raised portions 26 can also be different at different longitudinal locations of the shaft 12. In addition, the dimensions and/or shapes of each raised portion in a given axial cross-section can be different from one another. The changes in geometry of the outer surface 26 of the inner member 24 can occur gradually (linearly, curvilinearly, or any other type of gradual change) along the entire length of the fluid flow lumen, gradually along only a portion of the fluid flow lumen, or the changes can occur in step changes.

Figure 3:
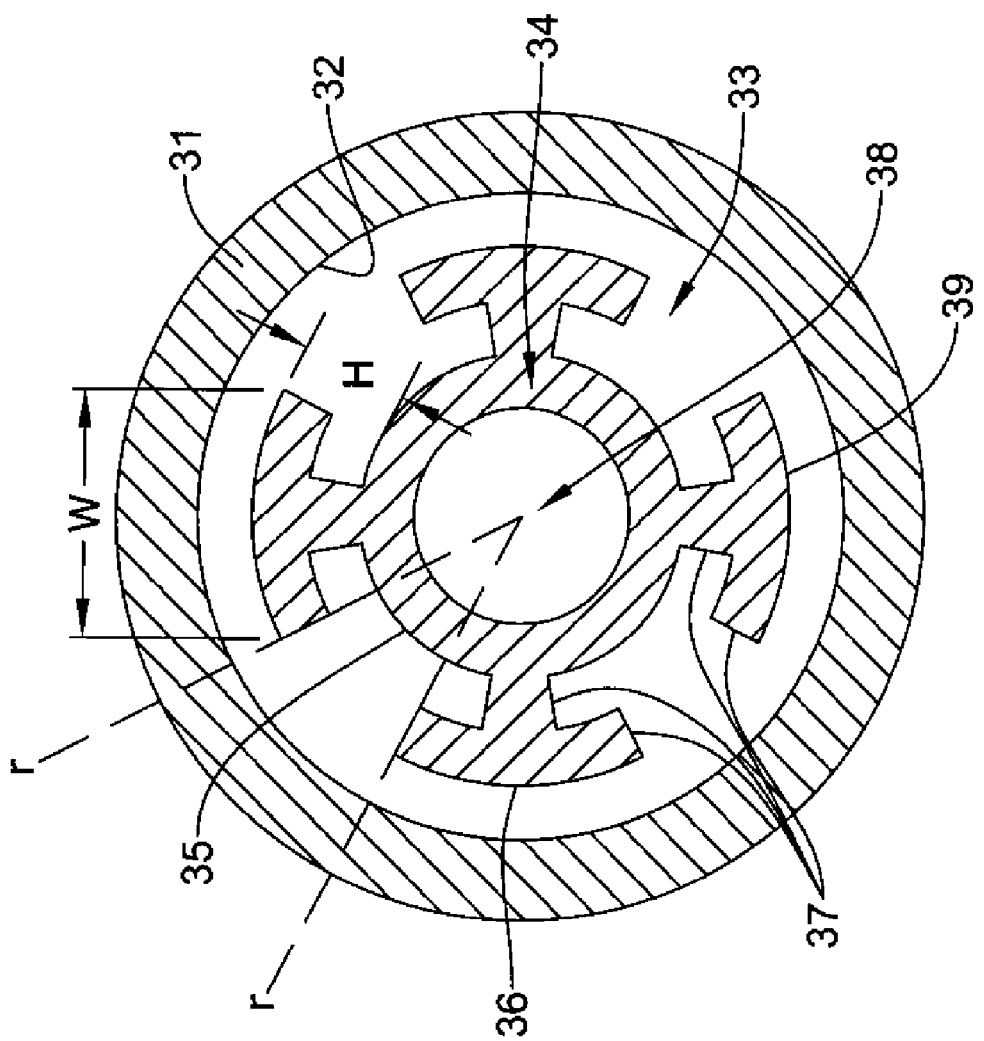
FIG. 3 is a cross-sectional view of a portion of the shaft of another embodiment with raised portions formed on the inner member.

FIG. 3 is an axial cross-section of another embodiment of the current invention. This embodiment is an example of an alternate shape of the raised portions. The raised portions 36 in FIG. 3 are shaped like one-half of an "I-beam" shape. The number, dimensions, and shapes of these raised portions can be similar to those described with respect to FIG. 2 above. The interaction and/or connection between the inner and outer members can also be similar to that described with respect to FIG. 2. The shape of the raised portions 36 can also be designed to maintain an open area for fluid flow between and around the raised portions 36, even where the inner and outer members might be in contact. The raised portions 36 can also be varied along the length of the shaft 12, or can extend for only a portion of the shaft 12, in a manner similar to that described with respect to FIG. 2 above. Further, the shaft designs of FIG. 3 can be combined with the designs described above with respect to FIG. 2. The designs can be combined in one cross-section of the shaft, and/or the shaft can incorporate different cross-section designs at different portions along the shaft.

Figure 4:
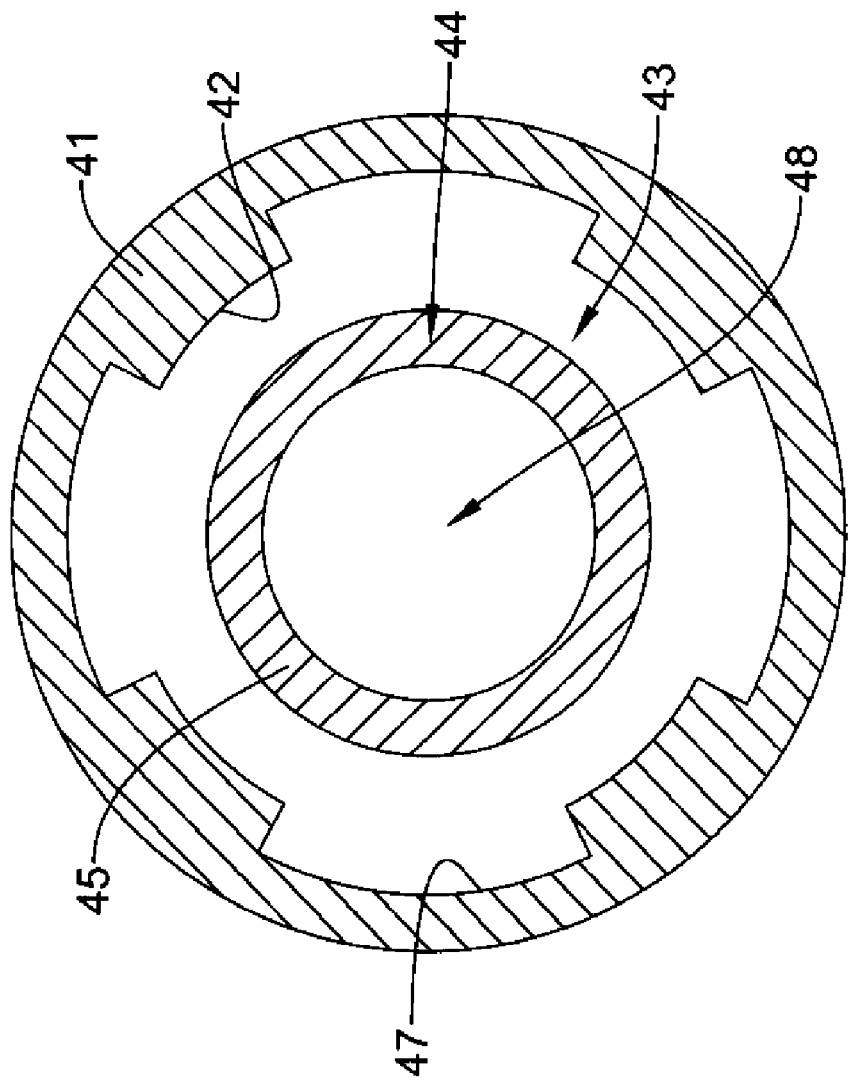
FIG. 4 is a cross-sectional view of a portion of the shaft of another embodiment with raised portions formed on the outer member.
Figure 5:
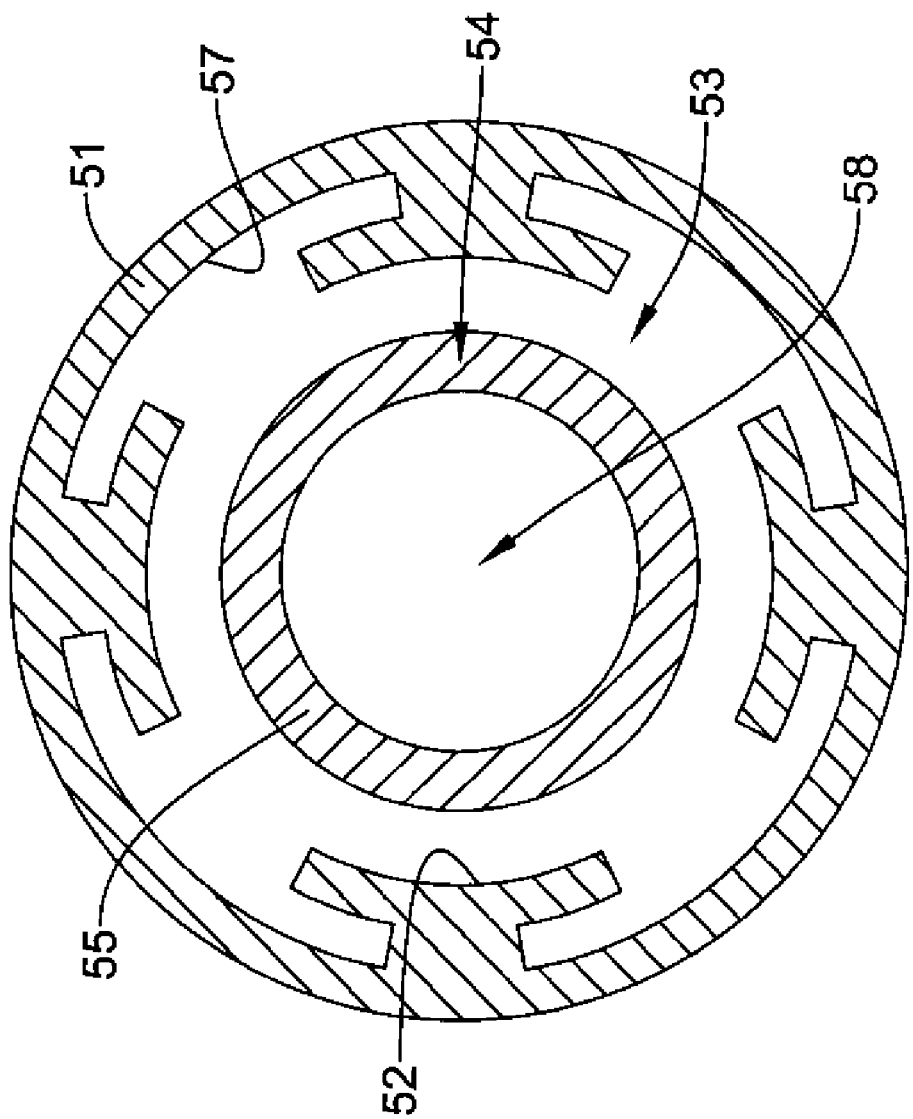
FIG. 5 is a cross-sectional view of a portion of the shaft of another embodiment with raised portions formed on the outer member.

FIGS. 4 and 5 show axial cross-sections of shafts of two additional embodiments of the current invention. In FIG. 4, the raised portions 42 are placed on the inner surface 47 of the outer member 41, rather than on the inner member 44. In FIG. 5, the raised portions 56 are placed on the inner surface 57 of the outer member 51, but have a one-half "I-beam" shape much like that described with respect to FIG. 3 above. These raised portions (42, 52) can be designed to maintain an open fluid flow pathway along the entire length of the fluid flow lumen, even where the inner and outer members may come in contact. The interaction and/or connection between the inner and outer members can also be similar to that described with respect to FIG. 2. Again, the shapes, dimensions, and number of raised portions can be altered, can vary along the length of the shaft, and can extend for different portions of the shaft length as described with respect to FIG. 2 above. Further, the shaft designs of FIGS. 4 and 5 can be combined with the designs described above with respect to FIGS. 2 and 3. The designs can be combined in one cross-section of the shaft, and/or the shaft can incorporate different cross-section designs at different portions along the shaft.

Figure 6:
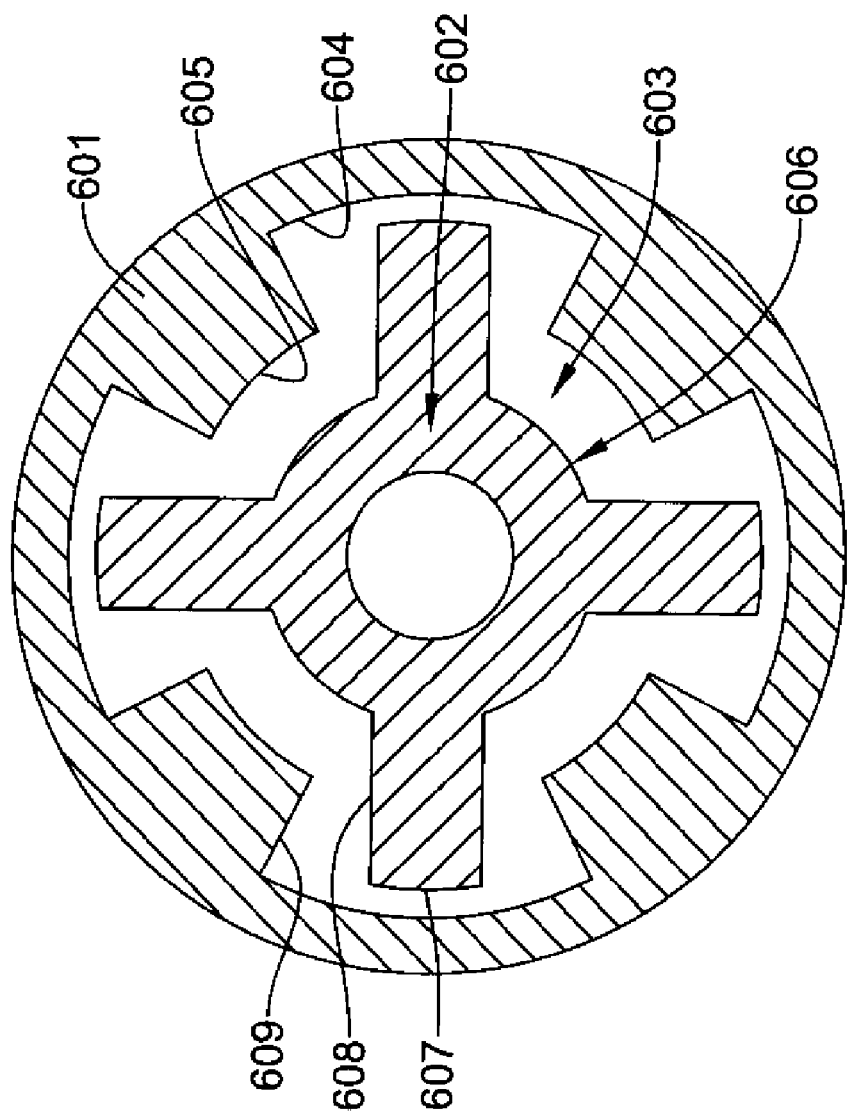
FIG. 6 is cross-sectional view of a portion of the shaft of another embodiment with raised portions formed on both the inner and outer members.
Figure 7:
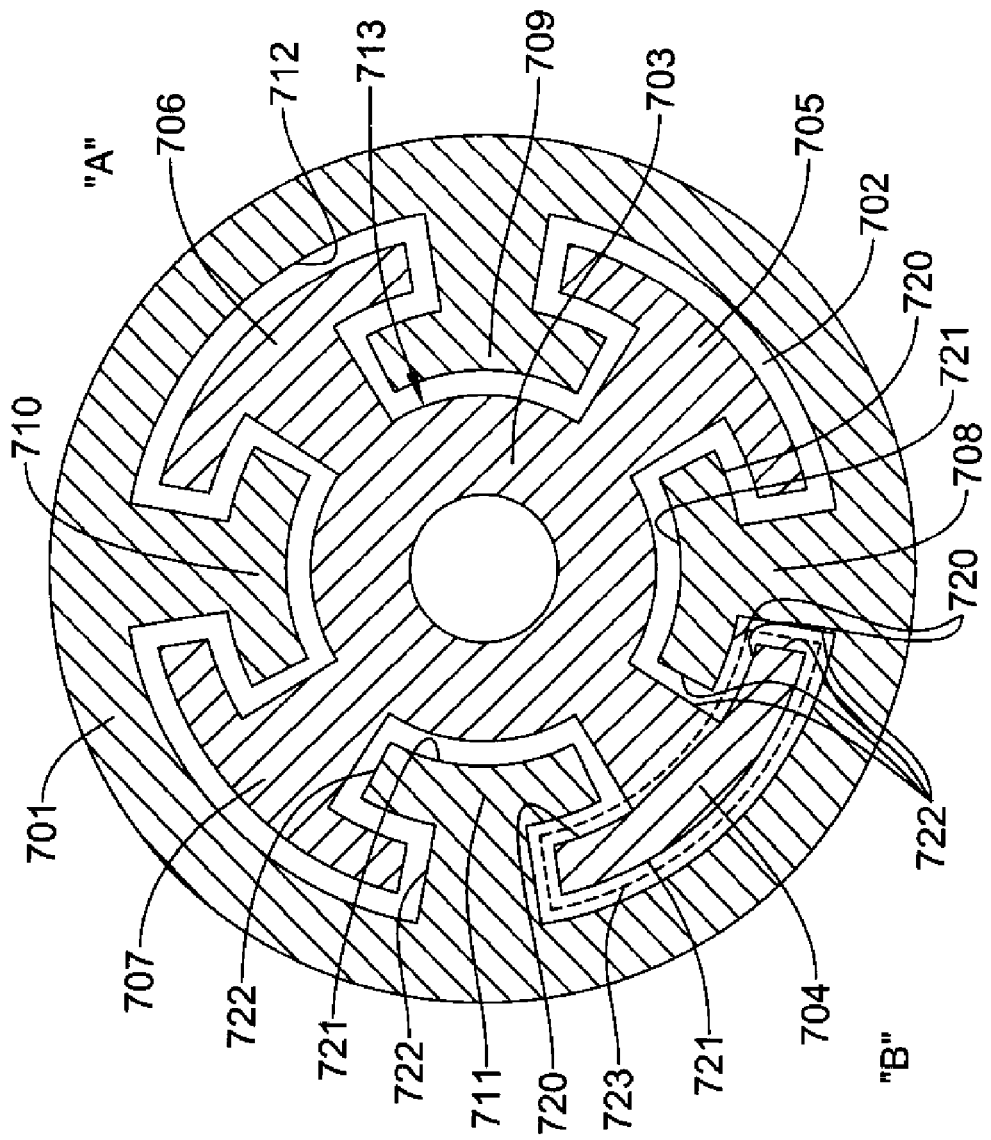
FIG. 7 is cross-sectional view of a portion of the shaft of another embodiment with raised portions formed on both the inner and outer members.

FIGS. 6 and 7 are two additional embodiments of the current invention that show some possible combinations of the designs described above. In both of these figures, both the inner surface of the outer member and the outer surface of the inner member have raised portions. These raised portions can interact in order to provide for different amounts and different types of shaft strengths.

In the embodiment shown in FIG. 6, inner member 602 can be disposed within outer member 601. A fluid flow lumen 603 can be formed in a space between the inner and outer members. Raised portions 605 can be formed on the outer member inner surface 604. In addition, raised portions 607 can be formed on the inner member outer surface 606. Similar to the interactions described above with respect to FIGS. 2-7, the raised portions 607 of the inner member can contact the outer member inner surface 604 and the raised portions 605 of the outer member can contact the inner member outer surface 606 when the shaft is deflected or otherwise subjected to forces.

In the embodiment of FIG. 6, the raised portions 607 of the inner member can have sides 608. In addition, the raised portions 605 of the outer member can have sides 609. If the inner and outer members are rotated with respect to one another (such as when the shaft is placed under torque), the sides (608, 609) can come in contact with one another, facilitating the transfer of torque down the length of the shaft. Further, the outer diameter of the inner member (including the raised portions) can be sufficiently large (for example, of sufficiently large height) to ensure that the raised portions 607 of the inner member remain between the raised portions 605 of the outer member. In addition, the raised portions (605, 607) can be shaped and designed, and can interact in such as a manner as to preserve a fluid flow pathway down the length of the fluid flow lumen.

The shapes, dimensions, and number of raised portions on each elongate member can be altered, can vary along the length of the shaft, and can extend for different portions of the shaft length as described with respect to FIG. 2 above. The interaction and/or connection between the inner and outer members can also be similar to that described with respect to FIG. 2. Further, the shaft designs of FIG. 6 can be combined with the designs described above with respect to FIGS. 2, 3, 4 and 5. The designs can be combined in one cross-section of the shaft, and/or the shaft can incorporate different cross-section designs at different portions along the shaft.

FIG. 7 shows an example that is similar in many respects to FIG. 6. FIG. 7 has raised portions that interlock with one another. Although they could be other shapes that can interlock with one another, FIG. 7 uses the one-half "I-beam" shape that is described above with respect to FIG. 3. In FIG. 7, inner member 703 is disposed within outer member 701, and a fluid flow lumen 702 is defined between the inner and outer members. The outer member inner surface 712 can have raised portions (708, 709, 710, 711) disposed on it, while inner member outer surface 713 can have raised portions (704, 705, 706, 707) disposed on it.

These inner and outer raised portions can be designed to interlock with one another. An example of this interlocking is shown in FIG. 7. Raised portion 704 can occupy the space denoted by the dotted line, which is defined by the raised portions (708, 711) and the portion of the outer member inner surface between raised portions (708, 711). The raised portions have a top, bottom portions and sides. As an example, the tops of raised portions 704 and 708 are marked 721, the bottoms are marked 720, and the portions that make up the sides of each are marked 722.

This interlocking design can allow for interaction between the raised portions when torque is placed on the shaft (as described with respect to FIG. 6 above), but the interlocking can also cause the inner and outer members to interact in other ways. For example, if forces (such as a sharp bend) cause the inner member to move within the outer member toward the letter "A" in FIG. 7, the raised portion 706 may move toward and eventually contact the inner surface of the outer member. The raised portions 710 and 709 can also move toward and eventually contact the outer surface of the inner member. The bottom of raised portion 704 can also move toward and eventually contact the bottoms of raised portions 708 and 711, which can essentially pull on the side of the outer member that is designated "B." The raised portion 704 can be described as radially interlocked with the raised portions 708 and 711. In this way, the inner and outer members can cooperate more fully, allowing for a strong, kink resistant shaft.

The raised portions can be shaped and designed in order to maintain a fluid flow pathway along the entire length of the fluid flow lumen. The shapes, dimensions, and number of raised portions on each elongate member can be altered, can vary along the length of the shaft, and can extend for different portions of the shaft length as described with respect to FIG. 2 above. The interaction and/or connection between the inner and outer members can also be similar to that described with respect to FIG. 2. Further, the shaft designs of FIG. 7 can be combined with the designs described above with respect to FIGS. 2, 3, 4, 5 and 6. The designs can be combined in one cross-section of the shaft, and/or the shaft can incorporate different cross-section designs at different portions along the shaft.

Other embodiments of the current invention use alternate structures to transfer forces down the shaft of the medical device while maintaining an open fluid lumen. In some embodiments, the inner and outer members are designed and configured to contact one another in a transition area. In the transition area of some embodiments, changes in dimension of the inner member can interact with changes in dimension of the outer member, causing a physical interference that can facilitate force transfer down the shaft. In addition, shafts could contain multiple transition areas, for example 2, 3, 4, or 5 transition areas.

Figure 8:
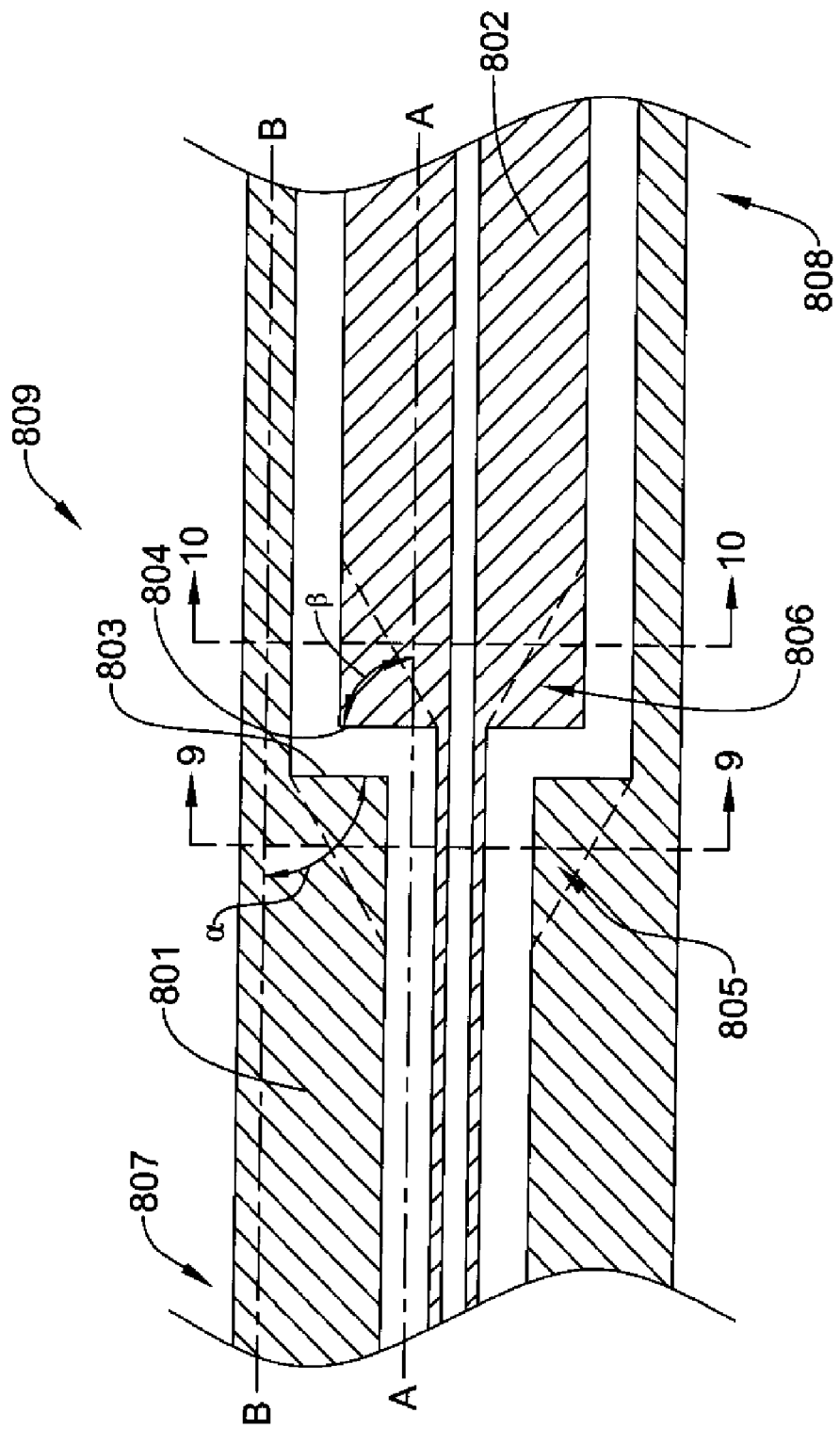
FIG. 8 is a cross-sectional view of a transition zone of one embodiment where the inner and outer members interact in a transition area.

For example, in FIG. 8, the shaft has a transition area 809, with a proximal area 807 and a distal area 808. Proximal of the transition area 809, the outer member 801 has a small inner diameter relative to the inner diameter of the outer member 801 distal of the transition area 809. The transition between the larger and smaller inner diameters in the outer member 801 creates an inner force transfer surface 803. This inner force transfer surface 803 can be oriented at any angle ($\alpha$) relative to an axis B-B running down the length of the outer wall of the outer member 801, such as an acute, perpendicular or obtuse angle. FIG. 8 shows the force transfer surface 803 oriented at a perpendicular angle relative to the axis B-B.

Distal of the transition area 809, the inner member 802 has a large outer diameter relative to the outer diameter of the inner member 802 proximal of the transition area 809. The transition between the larger and smaller inner diameters in the inner member 802 creates an inner force transfer surface 804. This inner force transfer surface 803 can be oriented at an angle ($\beta$) relative to an axis A-A running down the center of the inner member 802, such as an acute, perpendicular or obtuse angle. FIG. 8 shows the force transfer surface 803 oriented at a perpendicular angle relative to the axis A-A. The inner and outer force transfer surfaces (803, 804) can be oriented at complementary angles, and can be located a longitudinal distance from one another. In FIG. 8, the angles would be complimentary when the angles ($\alpha$, $\beta$) are substantially the same so that the inner and outer force transfer surfaces come in substantially continuous contact with one another. As the outer member is pushed, the outer and inner force transfer surfaces can move toward, and eventually contact, one another. (It is also envisioned that the force transfer surfaces could be in contact with one another before forces act one the shaft.) In this manner, the inner member can effectively assist in the transfer of forces down the shaft.

In other embodiments, the inner member can transition from a small outer diameter distal of the transition area to a relatively larger diameter proximal of the transition area. The outer member can have a small inner diameter distal of the transition area relative to the inner diameter of the outer member proximal of the transition area. This design could essentially be the mirror image of the design shown in FIG. 8, and could be similar in all other respects to the description of FIG. 8. If multiple transition areas are included in a shaft design, the shaft can include one or more transition areas like that shown in FIG. 8, one or more mirror image transition area designs described in this paragraph, or both.

Effective contact between the inner and outer force transfer surfaces (803, 804) can allow for efficient transfer of forces down the shaft, but could in some cases also cause the fluid flow lumen to be sealed off or restricted. In order to facilitate the transfer of fluid down the shaft, cut-outs (e.g., 805, 806) can be created that will allow fluid to flow through the transition area even when the force transfer surfaces (803, 804) are in contact. In FIG. 8, the cut-outs consists of two wedge-shaped pathways in each elongate member. The transition area could also consist of 1, 3, 4, 5, 6, 7, or 8 cut-outs or force transfer surfaces, or both in each elongate member. Additional embodiments could include other structures to maintain a fluid flow pathway through the transition area in place of, or in addition to, the cut-outs. For example, the force transfer surfaces could be made uneven so that contact between the inner and outer force transfer surfaces do not seal off the fluid flow lumen.

The shaft can incorporate any of the designs described above with respect to FIG. 2, 3, 4, 5, 6, or 7, or any of the combinations of designs described above. For example, a shaft design described above could be used proximal and/or distal of the transition area 809. The designs can be combined in one cross-section of the shaft, and/or the shaft can incorporate different cross-section designs at different portions along the shaft.

Figure 10:
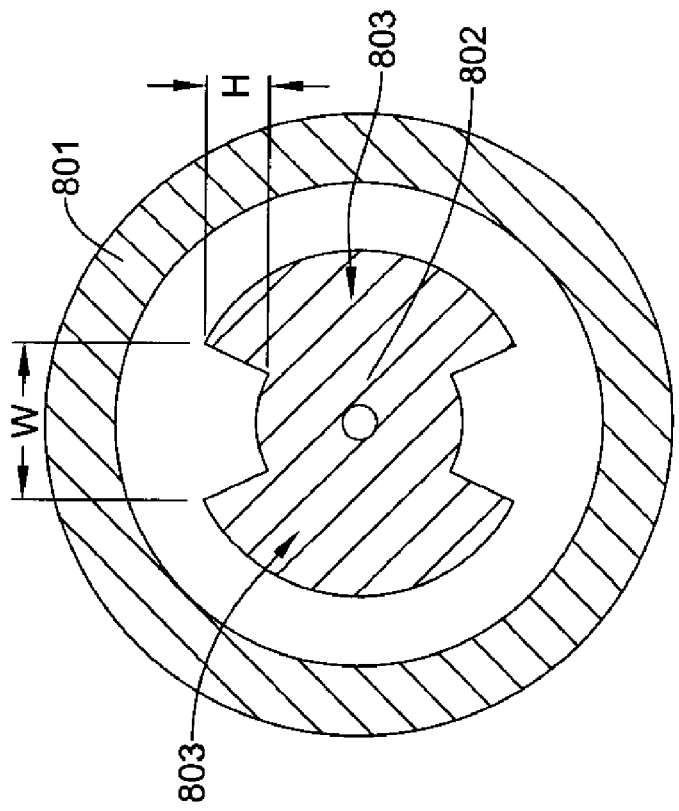
FIG. 10 is a cross-sectional view of a transition zone of one embodiment.
Figure 9:
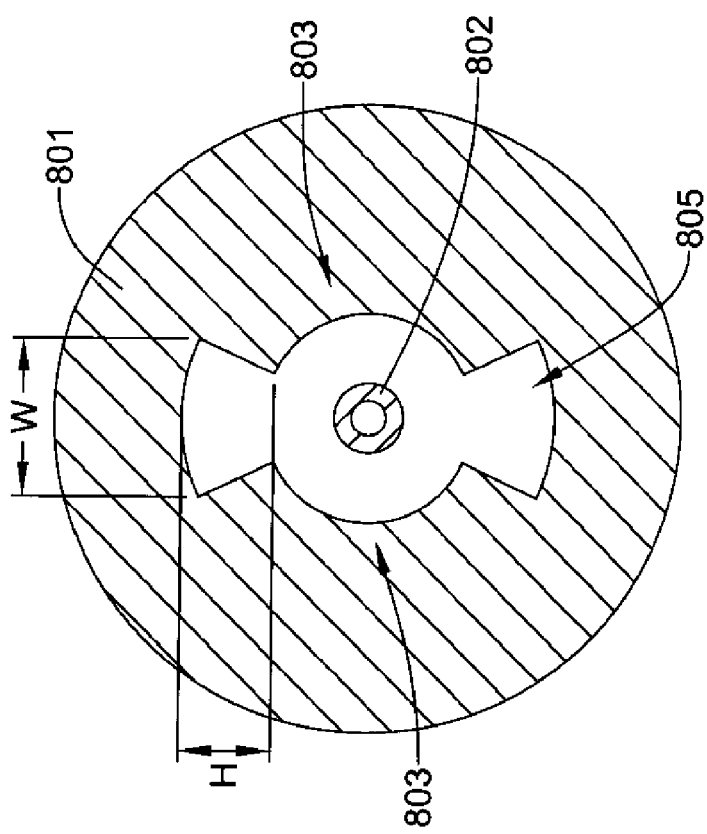
FIG. 9 is a cross-sectional view of a transition zone of one embodiment.

FIGS. 9 and 10 show axial cross-sections of the shaft of FIG. 8. FIG. 9 is a cross-section taken in a proximal portion of the transition area 809. FIG. 10 is a cross-section taken in a distal portion of the transition area 809. The cut-outs (805, 806) can be aligned with one another to create an efficient fluid pathway through the transition area 809. In addition, the force transfer surfaces (803, 804) can be aligned as well, providing for good force transfer between the outer and inner members. The cut-outs (805, 806) and the force transfer surfaces (803, 804) can be aligned by attaching the inner and outer members at points proximal and/or distal of the transition area, or the inner and outer members can be shaped or configured such that they cannot turn relative to one another (or cannot turn enough to prevent engagement of the cut-outs and the force transfer surfaces).

For example, both the inner and outer members could be shaped other than round (such as oval, square, triangular, rectangular, or other shape), and the inner member sized to prevent the inner member from being turned inside the outer member. As another example, the inner member could have a protrusion distal or proximal of the transition area that is positioned and shaped to fit into a receiving structure (such as a slot or one or more stops) on the inner surface of the outer member. (Alternatively, the protrusion could be disposed on the outer member and the receiving structure could be disposed on the inner member.) The interaction between the protrusion and the receiving structure can prevent rotation of the inner and outer members with respect to one another. As an example, a structure incorporating raised structures (either in one location or along all or a portion of the shaft) on both the inner and outer members could prevent the rotation of the inner member with respect to the outer member, (e.g., as described with respect to FIGS. 6 and 7 above).

Figure 11:
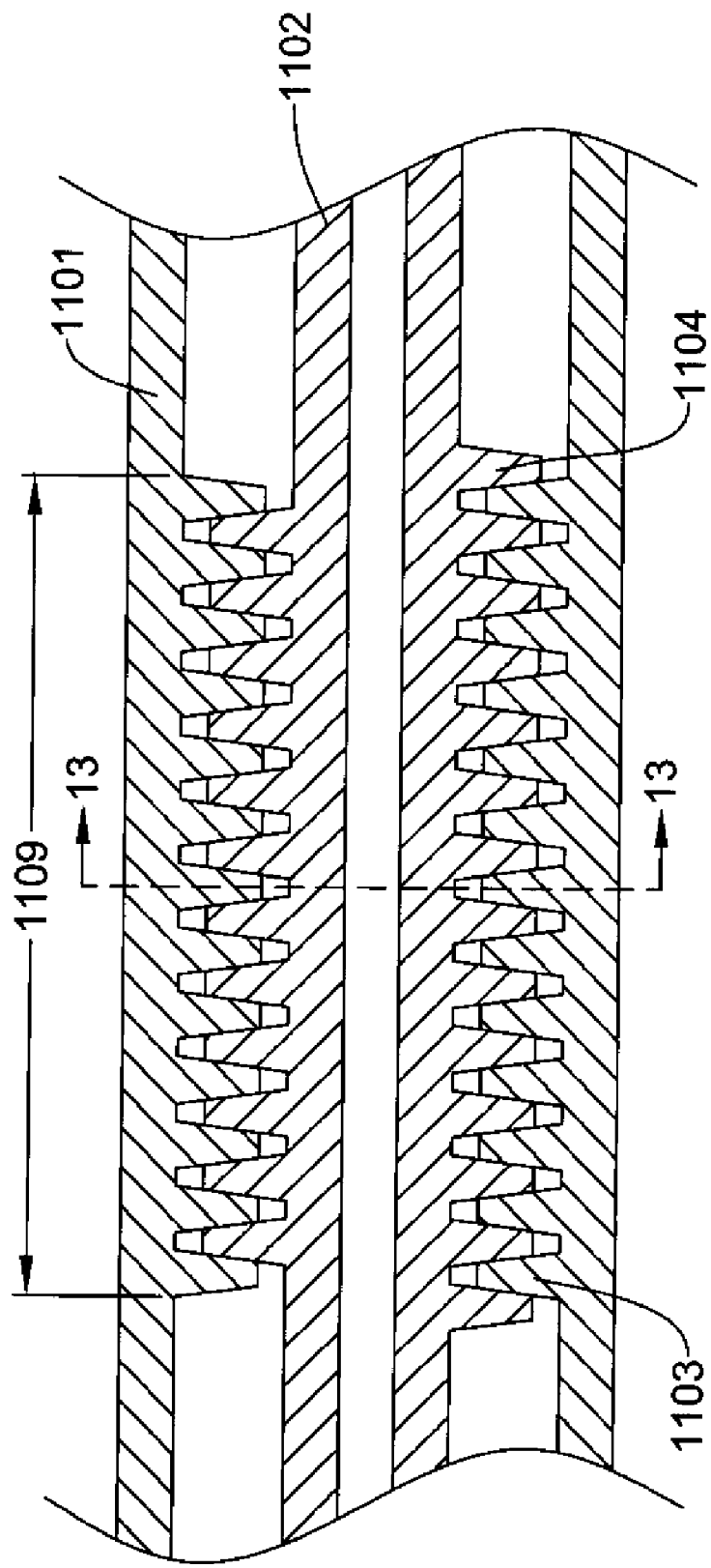
FIG. 11 is a cross-sectional view of a transition zone of another embodiment where the inner and outer members interact in a transition area.

In another embodiment of the current invention, the inner and outer members can interlock in a transition area by other means, such as a threaded interlock between the inner and outer members. In FIG. 11, an example of a threaded interlock is shown in longitudinal cross-section. The inner surface of outer member 1101 can have female threads 1103. In addition, the outer surface of the inner member 1102 can have male threads 1104. These threads can interact to effectively attach the inner and outer members to each other in the transition area 1109. This attachment can improve the transfer of forces down the length of the shaft.

Figure 12:
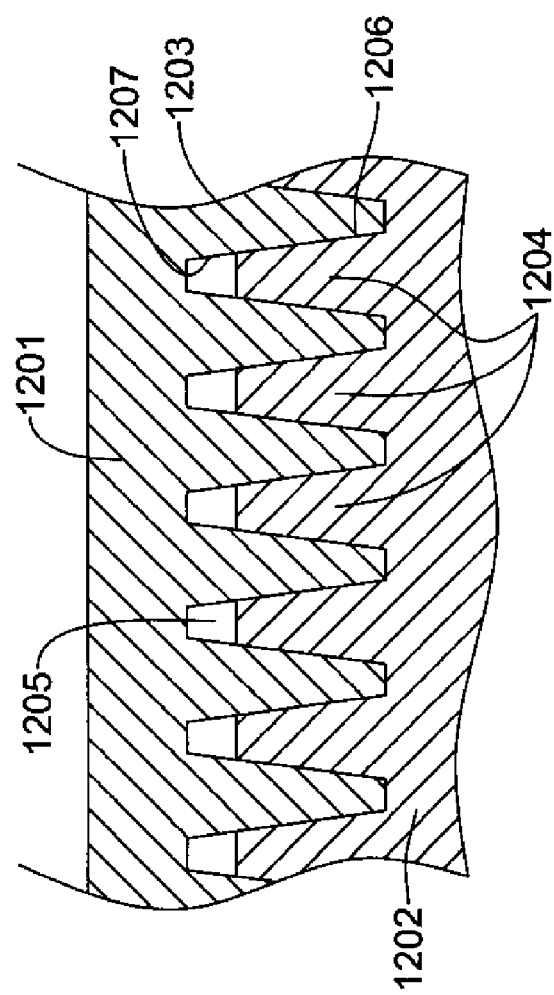
FIG. 12 is a cross-sectional view of threads of one embodiment.

The engagement of the female and male threads could also have a tendency to restrict or cut off the flow of fluids through the transition area 1109, depending on how tightly the threads mesh with one another. FIG. 12 shows one possible manner in which a fluid pathway could be maintained through a transition area when the threads are engaged with one another. One set of threads (here, the male set of threads 1204 on the inner member 1202) can be less deep relative to the other set of threads 1203. Thus, a spiral fluid pathway will be maintained between the top of the shorter threads 1204 and the inner surface of the outer member 1201 along the thread pathway. It is also envisioned that the female threads could be less deep relative to the male threads, creating a space between the top of the shorter threads and the inner surface of the inner member, or that both sets of threads would not fill the spaces between the corresponding threads.

Further, the sides of the threads (e.g., 1206, 1207) can mesh tightly. In another embodiment, the threads may not mesh tightly, thus forming a fluid flow pathway between the sides (e.g., 1206, 1207) of the teeth.

Figure 13:
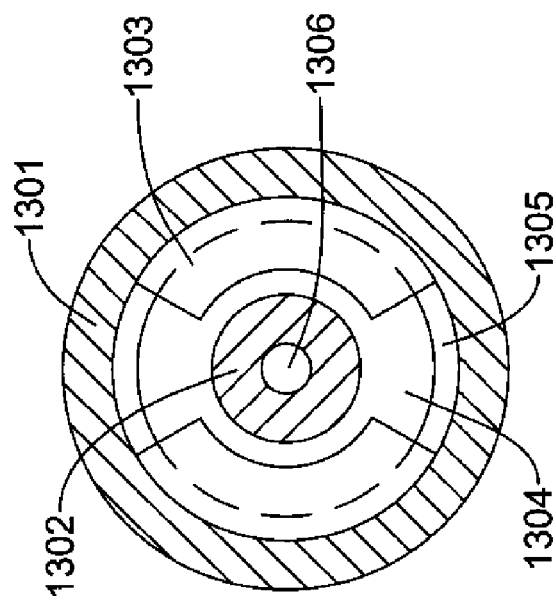
FIG. 13 is an axial cross-sectional view of threads of one embodiment.

Another embodiment, shown in FIG. 13, has portions of the threads removed in one or more cut-outs 1304. The outer diameter of the inner member 1302 (including the male threads) can be less than the inner diameter of the outer member 1301 (not including the female threads). Thus, there can be a fluid pathway maintained through the transition area through the cut-out between the top of the male threads and the inner surface of the outer member. When there is only one cut-out, the threads can fit sufficiently tightly into one another to prevent the inner member from moving within the outer member and blocking off the cut-out. As an alternative, there can be 2, 3, 4, 5, 6, 7, or 8 cut-outs. With more than one cut-out, the inner member can move within the outer member to block off some of the cut-outs, but other cut-outs will remain open, maintaining an open fluid pathway. The one or more cut-outs can also be formed through the inner member threads, or cut-outs can be placed in both the inner and outer threads.

The examples of the shaft designs above show a guidewire lumen defined by an inner member. The guidewire lumen may or may not be present in certain embodiments. In addition, the inner member can define multiple lumens, which can be suitable as fluid flow lumens, guidewire lumens, lumens for introducing other devices, or for any other uses known in the art. In addition, it is also contemplated that the shaft could comprise three elongate members, with two fluid flow lumens. The first fluid flow lumen could be defined between the inner and a middle elongate members, and the second fluid flow lumen could be defined between the middle and the inner elongate members. The design of these fluid flow lumens could be similar to any of the designs herein. For example, when looking to the design of the outer lumen, the outer and the middle elongate members could be analogous to the outer and inner members described in embodiments above, respectively. When looking to the design of the inner lumen, the middle and the inner members could be analogous to the outer and inner members described above, respectively. The guidewire or other lumen can also be defined by a space between two of the elongate members.

Additionally, the axial cross-sectional figures all show designs with a generally round, co-axial design. However, it is envisioned that cross-sections of the inner, the outer, or both members can be shapes other than round, for example oval, square, rectangular, pentagonal, hexagonal, or polygonal. It is also envisioned that the inner member need not be positioned co-axially with respect to the outer member. The inner member can be offset to one side, and could even be attached to one side of the outer member.

A variety of materials could be used in the construction of the medical device. Suitable materials for the elongate members of the shaft and the raised portions of these members include metals and metal alloys, polymeric material, composites of materials, or any other suitable material. Some examples of metal and metal alloys include stainless steel, such as 304V, 304L, and 316L stainless steel; alloys including nickel-titanium alloy such as linear elastic or superelastic (i.e., pseudoelastic) nitinol; nickel-chromium alloy; nickel-chromium-iron alloy; cobalt alloy; tungsten or tungsten alloys; MP35-N (having a composition of about 35% Ni, 35% Co, 20% Cr, 9.75% Mo, a maximum 1% Fe, a maximum 1% Ti, a maximum 0.25% C, a maximum 0.15% Mn, and a maximum 0.15% Si); hastelloy; monel 400; inconel 625; or the like; or other suitable material, or combinations or alloys thereof.

Examples of suitable polymeric material can include: poly (L-lactide) (PLLA), poly(D,L-lactide) (PLA), polyglycolide (PGA), poly(L-lactide-co-D,L-lactide) (PLLA/PLA), poly (L-lactide-co-glycolide) (PLLA/PGA), poly(D, L-lactide-co-glycolide) (PLA/PGA), poly(glycolide-co-trimethylene carbonate) (PGA/PTMC), polyethylene oxide (PEO), polydioxanone (PDS), polycaprolactone (PCL), polyhydroxybutyrate (PHBT), poly(phosphazene), polyD,L-lactide-co-caprolactone) (PLA/PCL), poly(glycolide-co-caprolactone) (PGA/PCL), polyanhydrides (PAN), poly(ortho esters), poly(phoshate ester), poly(amino acid), poly(hydroxy butyrate), polyacrylate, polyacrylamid, poly(hydroxyethyl methacrylate), polyurethane, polysiloxane and their copolymers, or mixtures or combinations thereof.

The inner and outer members of the shaft can be made from different materials, and different materials can be used for different longitudinal portions of the shaft. In addition, raised portions and the elongate members on which they are disposed can be made of differing materials.

The medical device can also be made compatible with a magnetic resonance imaging (MRI) procedure by including in the medical device only (or substantially only) materials that are compatible with MRI, or by including MRI compatible materials along at least a portion of the shaft. The medical device can also include portions or markers that are X-ray visible. Markers could be placed on a distal or proximal portion of a balloon, or on any other portion of the medical devices of this invention.

Another embodiment of the current invention is a method of using a medical device to transfer fluids from one location to another, including between two locations within a patient's body, delivering fluids into a patient's body, removal of fluids from a patient's body, or a combination thereof. A medical device in accordance with any of the embodiments described in this description can be introduced into a body lumen of a patient, and the distal end of the device is advanced to a location of interest. The medical device can be advanced on its own, or a guidewire or guide catheter can be advanced first, and the medical device advanced over or through the guidewire or guide catheter. Once the medical device is in place, a procedure that requires the introduction, removal and/or transfer of fluids can be performed by transferring fluids through the fluid flow lumen. One of the possible procedures would include the use of a balloon catheter, and the advancement of the balloon catheter to a site of interest. The balloon catheter can then be expanded using a fluid flow lumen of the medical device and, after the procedure (for example, angioplasty, stent placement, or a procedure including occlusion of a vessel) is complete, the balloon can be deflated by removing fluid through a fluid flow lumen.

Also disclosed is a method of making a shaft for an elongate medical device. In one production method, the shaft has an inner and an outer member, and at least one member has raised portions that extend along a portion of the shaft. The inner and outer members can be formed in one step (for example, by coextruding the two members), they can be formed separately and the inner member placed inside the outer member, or the outer member can be formed over the top of an existing inner member. The raised portions can be formed in the same step that forms the member on which they are placed, or the inner or outer member can be formed, and any raised portion(s) subsequently placed on or in the inner or outer member, respectively. The inner or outer member could also have the raised portions formed by removing material between the raised portions, for example by grinding or LASER ablation.

Another method of production could be to form an inner member from two or more elongate members. In this method, an inner member could be formed from two elongate members, and each elongate member could have a different outer diameter, with the joint formed at a transition area. An outer member could also be formed from two or more elongate members, each member with a similar outer diameter but differing inner diameters, with the joint formed at a transition area. The inner and outer members can then be placed together such that the larger diameter of the inner member and the smaller diameter of the outer member cause interference between the inner and outer members in a transition area. As an alternative, the transition in the inner diameter of the outer member and the outer diameter of the inner member can be formed by removing material from a portion of the inside of the outer member or by removing material from a portion of the outside of the inner member, or both. Also, the transition areas can have cut-outs formed in them in order to maintain a fluid flow lumen.

An alternate method of forming a medical device is to form threads on the outer surface of a transition area of an inner member, form threads on the inner surface of a transition area of an outer member, and place the inner member within the outer member such that the threads are in the same general longitudinal proximity along a shaft. The threads can also be shaped and configured to engage one another. The threads can be formed by placing additional material on the surfaces of the elongate members, or by removing material from the corresponding surfaces of the elongate members to create the threads.

Having thus described the several embodiments of the present invention, those of skill in the art will readily appreciate that other embodiments may be made and used which fall within the scope of the claims attached hereto. Numerous advantages of the invention covered by this document have been set forth in the foregoing description. Changes may be made in details, particular in matters of size, shape, and arrangement of parts without exceeding the scope of the invention. It will be understood that this disclosure is, in many respects, only illustrative.

What is claimed is:

1. An intracorporeal device comprising:
    an elongate shaft having inner and outer elongate members and a fluid flow lumen defined by a space between the inner and outer elongate members, the lumen in fluid communication with a balloon disposed on a distal end of the shaft;
    wherein an outer surface of the inner elongate member or an inner surface of the outer elongate member comprises at least one raised portion; and
    wherein the number of raised portions is varied along the length of the shaft, imparting a variable stiffness along the length of the shaft;
    wherein the sides of the at least one raised portion each extend substantially along a different radius extending out from an axis running down the center of the shaft.

2. The intracorporeal device of claim 1, wherein the raised portions have a height and a width, and wherein at least one dimension of the at least one raised portion is varied along the length of the shaft.

3. The intracorporeal device of claim 2, wherein the height of the raised portions is less in a distal section of the shaft than in a proximal section of the shaft.

4. The intracorporeal device of claim 2, wherein the width of the raised portions is less in a distal section of the shaft than in a proximal section of the shaft.

5. The intracorporeal device of claim 1, wherein raised portions extend the entire length of the member on which they are formed.

6. The intracorporeal device of claim 1, wherein there are four raised portions.

7. The intracorporeal device of claim 1, wherein the inner and outer members are tubular and are substantially coaxial with one another.

8. The intracorporeal device of claim 1, wherein the at least one raised portion is disposed on the outer surface of the inner elongate member or an inner surface of the outer elongate member, the top of the raised portion being in the shape of an arc, the arc substantially matching an arc defined by an inner surface of the outer elongate member or an adjacent surface of outer surface of the inner elongate member.

9. The intracorporeal device of claim 1, wherein the at least one raised portion is shaped like one-half of an I-beam.

10. The intracorporeal device of claim 1, comprising at least two raised portions, wherein the at least two raised portions are distributed on an elongate member at even intervals around the circumference of the elongate member.

11. The intracorporeal device of claim 1, further comprising at least two raised portions, wherein the raised portions have the same shape and dimensions.

12. An intracorporeal device comprising:
an elongate shaft having inner and outer elongate members and a fluid flow lumen defined by a space between the inner and outer elongate members, the lumen in fluid communication with a balloon disposed on a distal end of the shaft;
wherein an outer surface of the inner elongate member or an inner surface of the outer elongate member comprises at least one raised portion, the at least one raised portion having a width and a height; and
wherein at least one dimension of the at least one raised portion is varied along the length of the shaft, imparting a variable stiffness along the length of the shaft;
wherein the sides of the at least one raised portion each extend substantially along a different radius extending out from an axis running down the center of the shaft;
wherein the number of raised portions is varied along the length of the shaft.

\* \* \* \* \*